United States Patent [19]

Gellman

[11] Patent Number: 4,959,062
[45] Date of Patent: Sep. 25, 1990

[54] INTEGRATED SOFT SHELL RESERVOIR

[75] Inventor: Barry Gellman, Billerica, Mass.

[73] Assignee: C. R. Bard, Inc., Murray Hill, N.J.

[21] Appl. No.: 313,862

[22] Filed: Feb. 23, 1989

[51] Int. Cl.⁵ .............................................. A61B 19/00
[52] U.S. Cl. .................................... 604/403; 222/105; 141/314
[58] Field of Search ................................ 604/403–410; 222/386.5, 95, 105, 107; 248/95; 141/21–25, 114, 314, 39, 369, 375

[56]               References Cited
           U.S. PATENT DOCUMENTS

| Re. 32,065 | 1/1986 | Ralston, Jr. et al. | 604/408 |
| 3,031,104 | 4/1962 | Moskovitz | 222/386.5 |
| 3,117,695 | 1/1964 | Cox, Jr. | 222/105 |
| 3,173,579 | 3/1965 | Curie et al. | 222/105 |
| 3,592,365 | 7/1971 | Schwartzman | 222/209 |
| 3,883,046 | 5/1975 | Thompson et al. | 222/386.5 |
| 3,965,946 | 6/1976 | D'Alo | 141/51 |
| 4,049,033 | 9/1977 | Ralston, Jr. | 604/408 |
| 4,088,166 | 5/1978 | Miller | 604/408 |
| 4,090,541 | 5/1978 | Cammarata, III et al. | 150/0.5 |
| 4,096,897 | 6/1978 | Cammorata, III | 150/0.5 |
| 4,100,953 | 7/1978 | Miller | 150/0.5 |
| 4,308,904 | 1/1982 | Martin et al. | 604/408 |
| 4,320,789 | 3/1982 | Martin et al. | 222/107 |
| 4,424,190 | 1/1984 | Mather, III et al. | 422/46 |
| 4,466,888 | 8/1984 | Verkaart | 210/232 |
| 4,523,691 | 6/1985 | Larkin et al. | 220/206 |
| 4,700,871 | 10/1987 | Matsuo et al. | 222/107 |
| 4,798,578 | 1/1989 | Ranford | 604/4 |

FOREIGN PATENT DOCUMENTS 2910141  9/1979  Fed. Rep. of Germany ...... 604/408

Primary Examiner—John D. Yasko
Assistant Examiner—Adam J. Cermak
Attorney, Agent, or Firm—Dennison, Meserole Pollack & Scheiner

[57]                 ABSTRACT

A blood reservoir having a rigid shell portion defining a cavity and a flexible membrane attached with a liquid tight seal to the shell portion around the periphery of the shell. The assembled reservoir forming a liquid tight and variable volume with blood inlet and outlet ports integrally formed in the rigid shell portion. The shell portion further including a rib member laterally extending across the bottom of the rigid shell. The rib member is positioned adjacent the blood outlet port to force the flexible membrane to bridge the blood outlet port to further facilitate drainage from the reservoir.

3 Claims, 2 Drawing Sheets

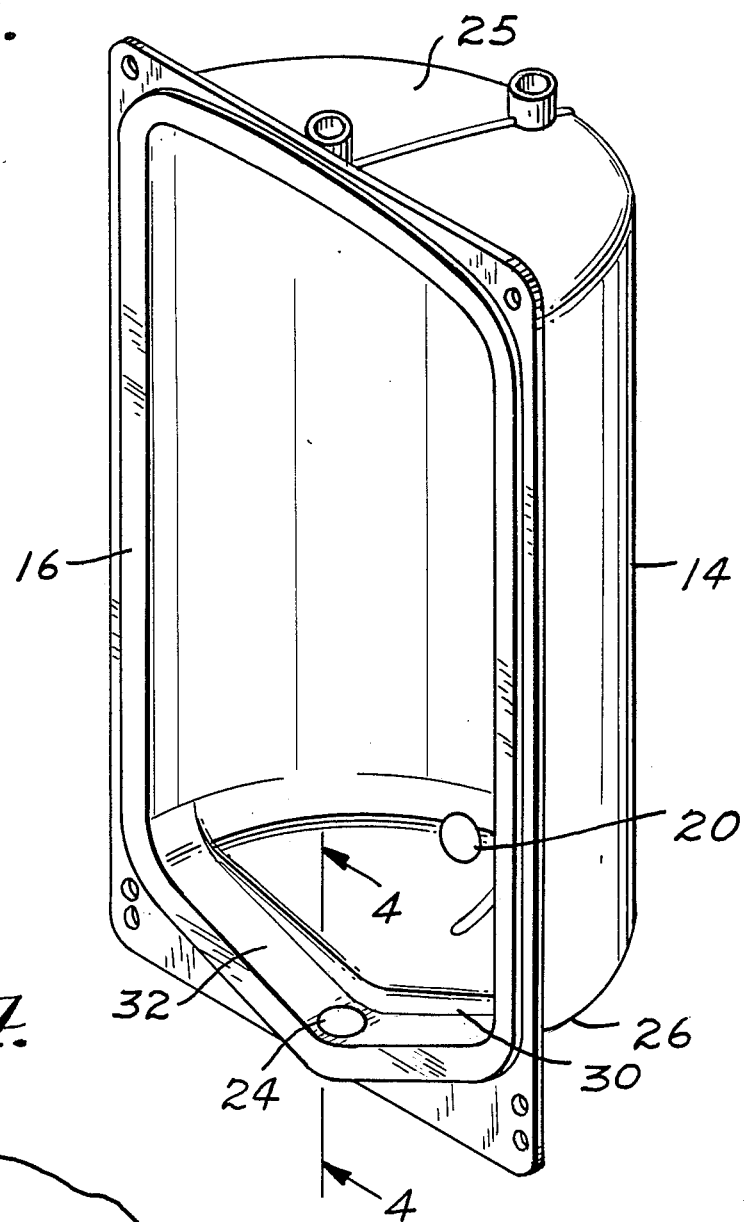
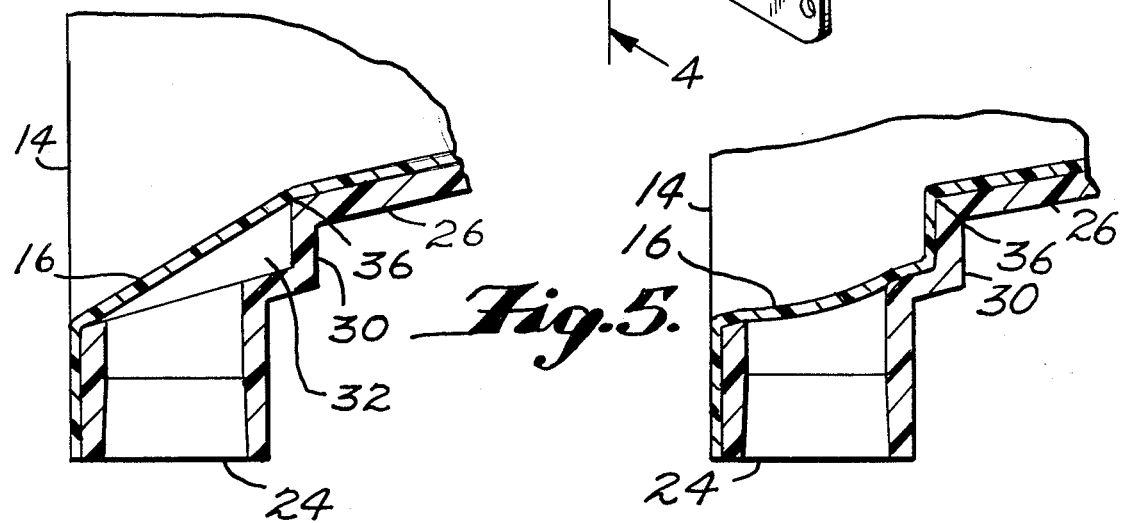

INTEGRATED SOFT SHELL RESERVOIR

BACKGROUND OF THE INVENTION

Field of the Invention

The invention relates to an integrated soft shell reservoir having a rib member positioned adjacent an outlet port to force an attached flexible membrane to bridge the outlet port and facilitate drainage of the reservoir.

Blood heaters, blood reservoirs and membrane oxygenators of various types are known and have been used in the past in the oxygenation of blood during surgery. One such type of unitary assembly with rigid reservoir, heater and a hollow fiber blood oxygenator is disclosed in U.S. Pat. No. 4,424,190.

In this system, and expansible blood reservoir is provided having a rigid self-supporting, concave shell and an integrally attached flexible membrane or complement member which forms a variable volume blood reservoir. The reservoir is constructed of transparent or translucent materials and arranged such that the blood in the reservoir is at all times visible to the technician during use for easy observation of the blood level. As is common in this device and others like it, the reservoir is provided with blood inlet means and blood outlet means. The blood outlet means is constructed with respect to size and location relative to the blood inlet means as to ensure a low exit of blood flow velocity.

A disadvantage with this type of reservoir is that the blood outlet port located at the base or bottom of the reservoir closes off and prevents blood drainage when a pucker forms in the receding flexible membrane. In other words, as the blood is draining out of the reservoir through the blood outlet port, the membrane begins to draw up and fold. As the fold gets in close proximity to the suction at the outlet port, the puckering membrane closes off the outlet port before the reservoir is completely drained.

SUMMARY OF THE INVENTION

To avoid the previously mentioned problem with the prior art devics, the present invention provides an integrated soft shell reservoir wherein a rib member is formed adjacent and transverse to the outlet port. This rib member forces the flexible membrane to bridge the opening of the outlet port. This construction prevents the inadvertent closing off of the exit port and allows full blood drainage out of the reservoir. The pucker in the membrane will not cause the hole of the outlet port to occlude because, as the reservoir continues to empty, the pucker or fold will spread along the ridge edge of the rib member. A noticeable absence of blood along this ridge indicates a visual seal.

An object of the invention is to provide a rib member positioned adjacent the blood outlet port for permitting the flexible membrane to bridge the blood outlet port.

Another object of the invention is to provide a rib member that extends laterally across the base of the reservoir.

A further object of the invention is to provide a rib member which prevents closing of the blood outlet port so that full blood drainage is allowed form the reservoir.

BRIEF DESCRIPTION OF THE DRAWINGS

FIG. 3 is a perspective view of the reservoir member;
and
FIGS. 4 and 5 are cross-sectional views of the blood outlet port taken along line 4—4 of FIG. 3.

DESCRIPTION OF THE PREFERRED EMBODIMENTS

Figure 1:
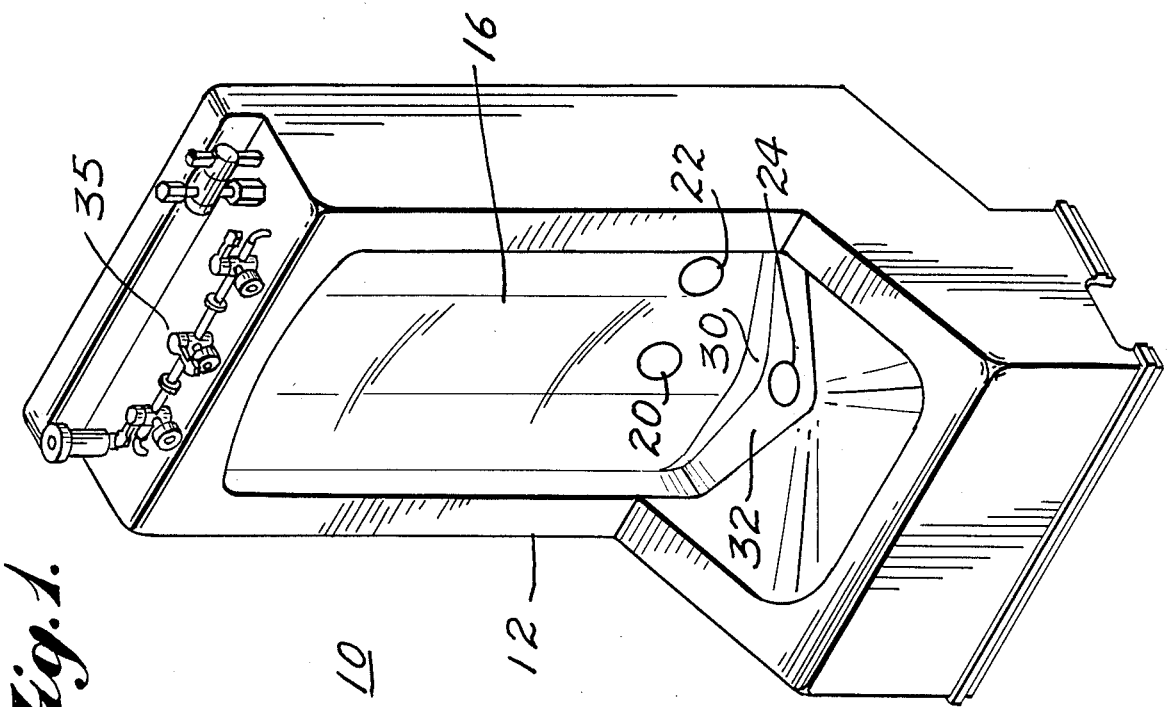
FIG. 1 shows the perspective view of the assembly.

FIG. 1 shows the HF 5400 system, generally indicated by numeral 10. The system 10 is connected at its base to a heater and an oxygenator which are both not shown since they are not part of the invention. The system 10 is comprised of a casing 12, a rigid plastic shell 14 and a flexible membrane member 16. The casing 12 encloses the plastic shell 14 and the membrane member 16. The shell 14 has two inlet ports, a venous inlet port 20 and a cardiotomy inlet port 22. The shell 14 further includes a blood outlet port 24 located at the base or bottom of the sloping wall of the shell 14.

Laterally extending across the base of the sloping wall 26 and adjacent to the blood outlet port 24 is a rib member 30 which forms a well 32 surrounding the blood outlet port 24. This construction at the base of the plastic shell 14 forms a semi-funnel area with the outlet port 24 forming the neck of the funnel.

Figure 2:
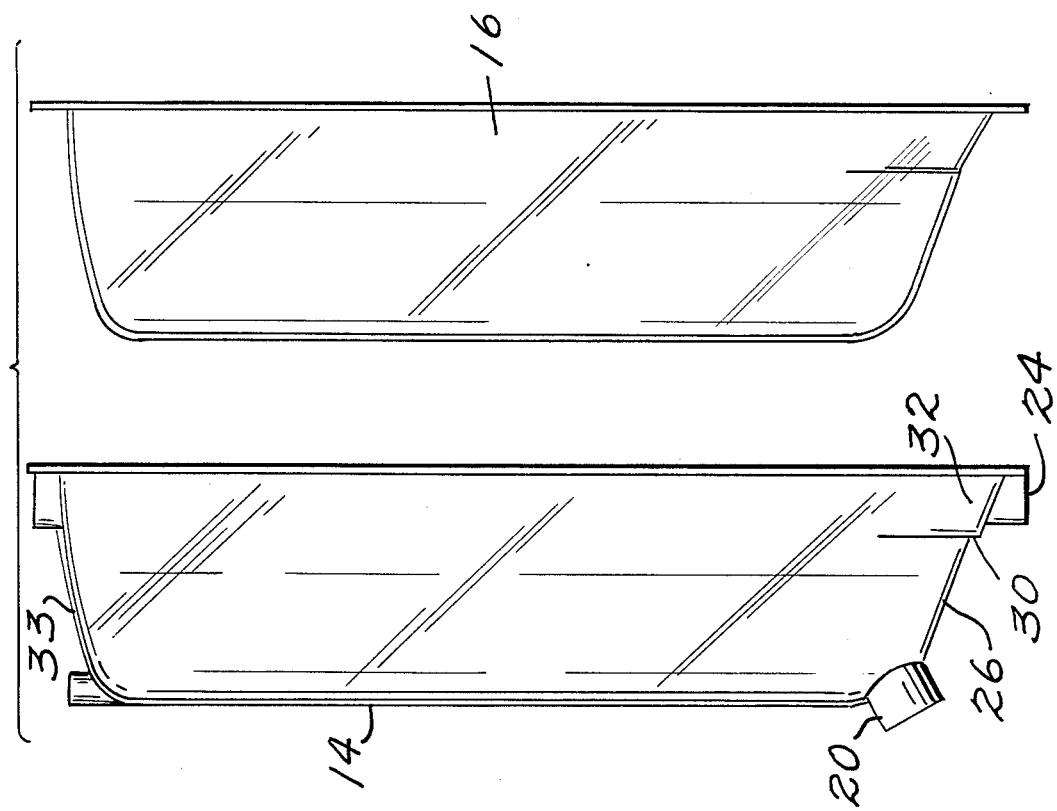
FIG. 2 is an exploded side view of the reservoir and membrane member.

FIG. 2 shows an exploded side view of the flexible membrane member 16 and the rigid hard shell 14. The flexible membrane member 16 is of a similar shape and size as that of the rigid shell 14. The flexible membrane 16 is formed from translucent or preferebly from transparent thin film of somewhat elastic, stress-resistant material that is blood compatible. It is semi-cylindrical in shape and is sized and shaped for attachment to the peripheral edges of the rigid shell 14 such that as the blood drains, the membrane 16 forms an intimate contact with the rigid wall surface of the shell 14.

The membrane 16 is fastened to the shell 14 by any suitable means which insures a continuous, liquid tight and air tight connection. The connection of the shell 14 and the membrane 16 forms a closed cavity which becomes a reservoir when pumped full of blood.

The shell 14 has a semi-cylindrical shape with the top surface forming a dome 33 and being connected to valves which are generally indicated by 35. Near the beginning or top of the sloping wall 26 are the inlet ports. The venous inlet port 20 and the cardiotomy inlet port 22 are positioned at an angle such that the blood entering the shell 14 will be directed away from the outlet port 24.

From the inlet ports, shell wall 26 slopes downwardly such that a semi-funnel is formed at the base of the shell 14. This sloping wall 26 and funnel area or well 32 help to provide further drainage of the blood through the outlet port 24.

Before the sloping wall 26 reaches the outlet port 24, the rib 30 protrudes outwardly away from the inside of the shell 14 and downwardly in the direction of the outlet port 24. The rib 30 further positions the outlet port 24 at the lowest point possible in the rigid shell 14 and prevents closing of the outlet port 24 during drainage as will be further explained with reference to FIGS. 3, 4 and 5.

FIG. 3 shows a perspective view of the invention. At the base of the funnel area or well 32 is the outlet port 24 wherein the blood is drawn out of the reservoir formed by the shell 14 and the membrane 16. The outlet port 24 is positioned below and adjacent to the rib member 30 which extends laterally across the base of the well 32. The outlet port 24 is closest to the edge of the shell and is at the lowest possible point of the well 32 to ensure the most efficient drainage of the reservoir. As the volumne of blood in the reservoir drops, the membrane 16 reverts to its natural semi-cylindrical shape. The membrane 16 begins hugging the inside of the shell 14. If the rib member 30 was not present, the membrane 16 would pucker and seal the outlet port 24 and not permit complete drainage. The rib 30, however, causes the membrane 16 to straddle or bridge the outlet port 24 until the reservoir formed by the shell 14 and the membrane 16 is empty of blood.

FIG. 4 is an enlarged partial sectional view of the rib member 30 taken along line 4—4 of FIG. 3. As blood is drained from the reservoir, the membrane 16 will touch the sloping wall 26 of the rigid shell 14. the rib member 30 will prevent the membrane 16 from collapsing over the outlet port 24 and actually force the membrane 16 to bridge the outlet port 24. Accordingly, as membrane 16 first touches the rib 30 at the ridge edge 36, the membrane 16 will progress left and right along the rib 30, permitting drainage of the reservoir to continue until complete drainage is achieved.

As illustrated by FIG. 5, which is an enlarged partial sectional view of the rib member 30 taken along line 4—4 of FIG. 3, when no fluid remains in well 32, membrane 16 stretches and closes over outlet port 24. A noticeable absence of blood along rib 30 indicates a visual seal.

Now, the membrane member 16 functions as a shut-off by preventing air from passing through outlet port 24 when the reservoir is drained via negative pressure from a pump, not shown. The membrane 16 bridges the outlet port 24 during low volume of blood in the reservoir to permit the fluid to flow from the sides of the wall of the shell 14 around the outlet port 24. The membrane 16 must be in intimate contact with the rib 30 along the sloping wall 26 until the well 32 has vanished. The membrane 16 is resilient and will stretch to completely shut-off the hole orifice of the outlet port 24. When the negative pressure is eliminated the membrane 16 resumes a rest state and opens outlet port 24 permitting flow.

While the invention has been described, disclosed, illustrated and shown in terms of certain embodiments or modifications which it has assumed in practice, the scope of the invention should not be deemed to be limited by the precise embodiments or modifications herein described, disclosed, illustrated or shown, such other embodiments or modifications as may be suggested to those having the benefit of the teachings herein being intended to be reserved, especially as they fall within the scope and spirit of the claims hereto appended.

What is claimed is:

1. A fluid reservoir, comprising:
    a rigid shell with an open face and an inner surface, said shell including; a top, a funnel shaped bottom including a lowermost point, and an interconnecting wall portion between said top and said bottom, an outlet opening defined through said funnel shaped bottom at said lowermost point for drainage of fluid from said reservoir, a peripheral edge extending around the open face of said shell, inlet means in said shell for introduction of fluid into said reservoir.
    a flexible membrane sealingly secured to said peripheral edge and extending across said open face and in overlying relation to said inner surface of said shell and defining therewith a fluid receiving chamber for reception of fluid introduced into said reservoir, said membrane being selectively expandable relative to said shell inner surface upon introduction of fluid, and intimately conformable with the inner surface of said shell upon drainage of fluid through said outlet opening, said membrane upon drainage of fluid through said outlet opening overlying and sealing said outlet opening, and
    means on said funnel shaped bottom for precluding sealing of said outlet opening until a complete drainage of fluid from said chamber between said shell inner surface and said membrane, said means for precluding sealing of said outlet opening including a ridge on said inner surface in said funnel shaped bottom adjacent to said outlet opening and extending beyond said outlet opening for selective support of said membrane above said outlet opening immediately adjacent thereto as fluid is drained and until drainage is complete, wherein said ridge tapers from a maximum height, relative to said inner surface, adjacent said outlet opening to opposed outer ridge ends merging with said inner surface laterally of said outlet opening and adjacent said wall portion.

2. The fluid reservoir as claimed in claim 1, wherein said outlet opening is between said peripheral edge and said ridge, said ridge defining a well in said funnel shaped bottom between said ridge and said peripheral edge, said lowermost point being defined in said well.

3. The fluid reservoir as claimed in claim 2, wherein said well is of maximum depth at said outlet opening and of minimum depth at the wall portion whereby as fluid is drained, the membrane will initially engage said ridge and will be precluded thereby from intimate engagement with said lowermost point within said well until a complete exhaustion of fluid from said well.

* * * * *